(12) United States Patent
Losev et al.

(10) Patent No.: US 9,125,867 B2
(45) Date of Patent: Sep. 8, 2015

(54) DIVERSION- AND/OR ABUSE-RESISTANT COMPOSITIONS AND METHODS FOR MAKING THE SAME

(75) Inventors: Mikhail Viktorovich Losev, Novosibirsk (RU); Alexandr Vasilievich Troitsky, Novosibirsk (RU); Michael Libman, Southampton, PA (US); Vadim Zolotarsky, Springfield, NJ (US)

(73) Assignee: Invincible Biotechnology, Southampton, PA (US)

( * ) Notice: Subject to any disclaimer, the term of this patent is extended or adjusted under 35 U.S.C. 154(b) by 483 days.

(21) Appl. No.: 12/660,268

(22) Filed: Feb. 24, 2010

(65) Prior Publication Data

US 2011/0207761 A1    Aug. 25, 2011

(51) Int. Cl.
| | |
|---|---|
| *A61K 31/44* | (2006.01) |
| *A01N 43/42* | (2006.01) |
| *A61K 31/135* | (2006.01) |
| *A01N 33/02* | (2006.01) |
| *A61K 31/137* | (2006.01) |
| *A61K 31/485* | (2006.01) |
| *A61K 9/20* | (2006.01) |
| *A61K 47/48* | (2006.01) |

(52) U.S. Cl.
CPC ............. *A61K 31/137* (2013.01); *A61K 9/2031* (2013.01); *A61K 9/2054* (2013.01); *A61K 31/485* (2013.01); *A61K 47/48192* (2013.01); *A61K 47/48853* (2013.01)

(58) Field of Classification Search
USPC .......................................... 514/646, 653, 649
See application file for complete search history.

(56) References Cited

U.S. PATENT DOCUMENTS

| | | | |
|---|---|---|---|
| 5,591,738 A | 1/1997 | Lotsof | |
| 5,686,253 A | 11/1997 | Skold et al. | |
| 7,250,422 B2 | 7/2007 | Jang et al. | |
| 7,375,082 B2 | 5/2008 | Mickle et al. | |
| 7,399,488 B2 | 7/2008 | Hirsh et al. | |
| 2003/0118641 A1 | 6/2003 | Maloney et al. | |
| 2004/0157784 A1* | 8/2004 | Chopdekar et al. ............. 514/23 |
| 2005/0176646 A1 | 8/2005 | Mickle et al. | |
| 2005/0266070 A1 | 12/2005 | Mickle et al. | |
| 2006/0003010 A1 | 1/2006 | Echanagorria et al. | |
| 2006/0014697 A1 | 1/2006 | Mickle et al. | |
| 2006/0057206 A1 | 3/2006 | Wong et al. | |
| 2007/0166416 A1 | 7/2007 | Palu et al. | |
| 2008/0020032 A1 | 1/2008 | Crowley et al. | |
| 2008/0069871 A1 | 3/2008 | Vaughn et al. | |
| 2008/0075771 A1 | 3/2008 | Vaughn et al. | |
| 2008/0076789 A1 | 3/2008 | Stinchcomb et al. | |
| 2008/0206161 A1 | 8/2008 | Tamarkin et al. | |
| 2009/0061011 A1* | 3/2009 | Talton ........................ 424/501 |
| 2009/0274759 A1 | 11/2009 | Bar-Shalom et al. | |
| 2012/0164228 A1* | 6/2012 | Suplie et al. .................. 424/489 |

FOREIGN PATENT DOCUMENTS

| | | |
|---|---|---|
| EP | 1212061 | 10/2004 |
| WO | 2007087452 | 2/2007 |
| WO | WO 2007039262 | 4/2007 |
| WO | 2008024490 | 2/2008 |
| WO | 2008033351 | 3/2008 |
| WO | WO 2008086804 A2 * | 7/2008 |

* cited by examiner

*Primary Examiner* — Shirley V Gembeh
(74) *Attorney, Agent, or Firm* — Pharmaceutical Patent Atty's LLC

(57) ABSTRACT

A composition formulated for diversion- and/or abuse-resistance, includes at least one active pharmaceutical ingredient (API), each present in an acidic form, a first compound capable of coupling to the acidic form of the API to form a complex, where the resulting complex is resistant to separation by conventional separation methods, and a second compound capable of preferentially coupling to the first compound to thereby release the API from the complex.

34 Claims, 10 Drawing Sheets

DIVERSION- AND/OR ABUSE-RESISTANT COMPOSITIONS AND METHODS FOR MAKING THE SAME

FIELD OF THE INVENTION

The present invention relates to the prevention of diversion and abuse of an active pharmaceutical ingredient, and more particularly a diversion- and/or abuse-resistant active pharmaceutical ingredient containing composition and methods for making the same.

BACKGROUND OF THE INVENTION

Certain pharmaceutical products such as painkillers and decongestants contain "active pharmaceutical ingredients" (API) that can offer a basis for illicit use including, but not limited to, abuse and diversion, such as ingredients providing a profound hallucinogenic effect, or precursors used in the production of drugs (e.g., narcotics). In addition, illicit use can occur with regard to ingredients that can be sold for profit in the illicit market. Among these active pharmaceutical ingredients are, for example, alkaloids such as ephedrine, pseudoephedrine, phenyl propanol amine, opiates such as oxycodone, morphine, hydrocodone, oxymorphone, and the like.

These active pharmaceutical ingredients require high levels of purification and are typically produced from plant extracts using sophisticated and expensive separation (e.g., extraction) technologies and chemical conversions that are available only to a select number of chemical and pharmaceutical companies. Their production is highly controlled by governmental agencies worldwide. However, clandestine efforts to produce these active pharmaceutical ingredients for illicit purposes (e.g., non-medical use) are a major problem and remain the focus of drug enforcement agencies.

Home-based production of these API in high quality directly from plant extracts is extremely difficult because of the sophisticated and expensive equipment required. However, their separation from commercially available pharmaceutical products is relatively simple. Accordingly, efforts are needed to make separation of API from commercial pharmaceutical products more difficult.

A number of API are further classified as "diversion" drugs and "recreational abuse" drugs. Diversion drugs are obtained from an illegal process wherein large quantities of pharmaceutical products containing API are processed to separate the API to make highly potent drugs (e.g., narcotics) for illegal trade. The separation process typically involves dissolving a large quantity of pharmaceutical products such as in the form of tablets in a small volume of a polar solvent, increasing the pH of the solution to precipitate the API, and separating the API with a non-polar solvent for further processing. Increasing the pH typically causes the salt form of the drug to convert to the free base form, which can be extracted by a non-polar solvent such as benzene, toluene, or methyl isobutyl ketone to separate the API from excipients and then utilizing the pure API for further synthesis.

A recreational abuse drug is a personalized use of a pharmaceutical product containing an API by a substance addict for non-medical use. There are several forms of recreational abuse, which include (a) extraction of the API from tablets using dissolution, pH adjustment, and separation for further personal use via intravenous injection, (b) multiple use of several dosage forms to increase the potency of a single application (overdose), and (c) crushing the tablets and inhaling the resulting powder (i.e., snorting) to bypass the digestive system and significantly increase the bioavailability of the API. Making API-containing pharmaceutical products diversion- and/or abuse-resistant is of critical importance to fighting the drug abuse epidemic.

It is desirable to formulate pharmaceutical products containing API in a manner in which the API becomes diversion-resistant (i.e., difficult to separate from the product by conventional means) and/or abuse-resistant (i.e., difficult to administer for a non-therapeutic or non-medical effect). There have been several attempts to formulate diversion-and/or abuse-resistant drugs. In general, these attempts are primarily directed towards developing drugs with a prolonged dissolution profile or include agents such as agonists, irritants, and gel forming compounds, which make it difficult to separate the API. None of these attempts, however, offer a real solution against diversion and recreational abuse and other illicit uses.

Accordingly, there is a need for diversion- and/or abuse-resistant compositions including pharmaceutical compositions, formulated in a manner that more effectively obstruct or impede illicit use of an active pharmaceutical ingredient (API). There is a further need to provide compositions containing API that hinder illicit use including separation of the API via conventional separation methods, making it difficult if not impossible for the illicit drug trade to isolate, purify and provide API for purposes of drug abuse or illicit drug trade.

SUMMARY OF THE INVENTION

The present invention relates generally to a system wherein an active pharmaceutical ingredient (API) can be delivered to a patient for prescribed medical use, but is diversion- and/or abuse-resistant to at least deter illicit use of the API. More specifically, there is provided in accordance with the present invention a pharmaceutical composition containing an API and an additive which prevents effective separation of the API by conventional separation techniques and/or prevents the administration of the API for a non-therapeutic or non-medical effect (e.g., recreational abuse). Methods of formulating the API-containing compositions and their use in delivering the API for prescribed medical use are also within the scope of the present invention.

In the world of drug abuse, illicit users have available relatively simple chemical and physical separation techniques as mentioned above. The present invention at least deters use of these simple chemical and physical separation techniques and thereby renders it very difficult if not impossible for illicit users to divert and/or abuse the API.

The composition of the present invention is specifically formulated to release the API under conditions of intended use. In particular, the present invention provides a novel combination of an API present in an acidic form with certain components or ingredients that together exhibit a unique set of chemical and physical properties useful for rendering the resulting composition diversion- and/or abuse-resistant. The compositions of the present invention including pharmaceutical compositions derived therefrom, include at least one API, each present in an acidic form.

The composition of the present invention further includes an additive comprising a first compound capable of coupling to the API present in an acidic form to form a complex in which the coupled API is resistant to separation through conventional separation methods, and a second compound capable of preferentially coupling to the first compound to thereby release the API from the complex under conditions of intended use. Preferably, the first compound is further capable of undergoing autooxidation and forming a suspension of fine particles in the presence of the API upon exposure to an increase in the pH (e.g., alkaline pH conditions) useful for enhancing the diversion-resistance of the composition. The composition of the present invention may be formulated into any suitable dosage form including, but not limited to, tablets, soft and hard capsules, gels, liquid or oral solutions, and the like.

As used herein, the term "separation" or "conventional separation method" refers to any method or technique by which the API could be separated from the pharmaceutical product by means typically available to illicit drug makers, users and the like, such as adsorption, chromatography, crystallization, extraction, filtration, precipitation, recrystallization, and the like.

As used herein the term "composition" or "pharmaceutical composition" refers to the combination of API in an acid form and other ingredients in any physical form including, but not limited to, a mixture, a complex, or the like, which renders the composition diversion- and/or abuse-resistant.

Once the acidic form of the API is complexed with the first compound, the API cannot be separated via any economically-feasible physical or chemical separation method such as by converting the salt form of the drug to the base form and then separating the API with a non-polar solvent. Preferably, the first compound is further capable of undergoing autooxidation and forming a suspension of fine particles in the presence of the API upon exposure to an increase in the pH (e.g., alkaline pH conditions) useful for enhancing the diversion-resistance of the composition of the present invention.

The first compound further preferably exhibits strong astringent properties including the capacity to shrink or constrict body tissues such as blood vessels and mucous membranes in warm-blooded animals including humans. The astringent properties of the first compound facilitate the prevention or deterrence of abusive uses of the present composition (e.g., snorting or overdosing). The constrictive activity induced by the first compound impedes or substantially reduces the absorption of the API under conditions of abuse. In this manner, the astringent properties of the first compound are useful for enhancing the abuse-resistance of the composition of the present invention.

In a preferred embodiment of the invention, the first compound is selected from polyphenols. Polyphenols exhibit the ability to complex with the acidic form of the API, the tendency to undergo autooxidation and form a suspension of fine particles in the presence of the API, upon exposure to an increase in the pH (e.g., alkaline pH conditions), and strong astringent properties including shrinkage or constriction of body tissue. Such polyphenols include hydrolyzable tannins such as gallic acid esters of sugars, and phenylpropanoids such as lignins, flavonoids, and condensed tannins. Particularly preferred polyphenols include tannic acid and gallic acid. The ability of the polyphenols to bind, precipitate and shrink proteins, makes these compounds effective against abuse, while the tendency to autooxidize at higher pH levels (e.g., alkaline pH conditions) makes them effective against diversion.

The coupling of the polyphenol to the acidic form of the API forms an insoluble complex that reduces the bioavailability of the API, and effectively renders the resulting composition diversion- and/or abuse-resistant. As previously discussed, the insoluble complex is resistant to separation by conventional methods thus making it difficult to isolate the API. To restore the bioavailability of the API, the second compound preferentially engages the first compound (e.g., preferentially binds to the first compound) under certain conditions. As a result, the API is released from the insoluble complex to perform its intended function. In a preferred embodiment of the present invention, the second compound is selected from water soluble polymers including, but not limited to, a polyalkyleneoxide such as, for example, polyethyleneoxide (e.g., polyethylene glycol).

The tendency for the polyphenol to autooxidize and form a suspension of fine particles in the presence of the API upon exposure to an increase in the pH (e.g., alkaline pH conditions) further renders the composition diversion-resistant. Under conditions of abuse, the ability of the polyphenol to shrink or constrict body tissue including the mucous membranes and blood vessels, significantly reduces the absorption of the API by the body such as through the mucosal membranes or the gastrointestinal lining.

In a further preferred embodiment of the present invention, there is provided a pharmaceutical composition for administration to a warm-blooded animal for release of an active pharmaceutical ingredient (API) for a therapeutic purpose, including a therapeutically effective amount of at least one API present in an acidic form, a first compound capable of coupling to the acidic form of the API to form a complex, wherein the complex is resistant to separation by conventional separation methods, a second compound capable of preferentially coupling to the first compound within the warm-blooded animal to thereby release the API from the complex, and a pharmaceutically acceptable carrier. Preferably, the first compound is selected from a polyphenol, and the second compound is selected from a water soluble polymer.

In another embodiment of the present invention, there is provided a method for administering an API to a warm-blooded animal, which includes the step of administering the pharmaceutical composition disclosed above.

In another embodiment of the present invention, there is provided a method for preventing diversion and/or abuse of an API, comprising the steps of obtaining a first compound capable of coupling to an API present in an acidic form to form a complex, wherein the complex is resistant to separation by conventional separation methods, obtaining a second compound capable of preferentially coupling to the first compound to thereby release the API from the complex, and admixing the first and second compounds with the API. Preferably, the first compound is selected from a polyphenol and the second compound is selected from a water soluble polymer.

In a preferred embodiment of the present invention, the API is selected from an alkaloid. Alkaloids include organic bases found in plants and are characterized by their specific physiological action and toxicity. They may be synthetically or semi-synthetically produced. Alkaloids may be related to various organic bases such as pyridine, quinoline, isoquinoline, pyrrole, and other more complicated derivatives. They contain nitrogen as part of the ring structure and have the general properties of amines.

The alkaloid may be selected, for example, from ephedrine, pseudoephedrine, phenyl propanol amine, opiates such as oxycodone, morphine, hydrocodone, oxymorphone, and the like. The composition of the present invention is specifically formulated to release the alkaloid under conditions of intended use.

In one aspect of the present invention, there is provided a composition, comprising:

(a) at least one active pharmaceutical ingredient (API), each present in an acidic form;

(b) a first compound capable of coupling to the acidic form of the API to form a complex, the complex being resistant to separation by conventional separation methods; and (c) a second compound capable of preferentially coupling to the first compound to thereby release the API from the complex.

In a further aspect of the present invention, there is provided a pharmaceutical composition for administration to a warm-blooded animal for release of an active pharmaceutical active (API) for a therapeutic purpose, comprising:

(a) a therapeutically effective amount of at least one API, each present in an acidic form;

(b) a first compound capable of coupling to the acidic form of the API to form a complex, the complex being resistant to separation by conventional separation methods;

(c) a second compound capable of preferentially coupling to the first compound within the warm-blooded animal to thereby release the API from the complex; and (d) a pharmaceutically acceptable carrier.

In a still further aspect of the invention, there is provided a pharmaceutical composition for administration to a warm-blooded animal for release of an active pharmaceutical ingredient (API) for a therapeutic purpose comprising a complex of an API present in an acidic form bound to a polyphenol and a water soluble polymer capable of preferentially binding to the polyphenol in said warm-blooded animal to thereby release the API from the complex.

In another aspect of the present invention, there is provided a pharmaceutical composition comprising a mixture, preferably in a dry form of an API present in an acidic form, a polyphenol and a water soluble polymer.

In still another aspect of the present invention, there is provided a method for administering an active pharmaceutical ingredient (API) to a warm-blooded animal comprising the step of administering a pharmaceutical composition comprising:

(a) a therapeutically effective amount of at least one API, each present in an acidic form;

(b) a first compound capable of coupling to the acidic form of the API to form a complex, the complex being resistant to separation by conventional separation methods; and (c) a second compound capable of preferentially coupling to the first compound within the warm-blooded animal to thereby release the API from the complex.

In another aspect of the present invention, there is provided a method for preventing diversion and/or abuse of an active pharmaceutical ingredient (API), comprising the steps of:

obtaining a first compound capable of coupling to an API present in an acidic form to form a complex, said complex being resistant to separation by conventional separation methods;

obtaining a second compound capable of preferentially coupling to the first compound to thereby release the API from the complex; and admixing the first and second compounds with the API.

In another aspect of the present invention, there is provided an additive for preventing diversion and/or abuse of an active pharmaceutical ingredient (API), comprising:

(a) a first compound capable of coupling to an API present in an acidic form to form a complex, said complex being resistant to separation by conventional separation methods; and (b) a second compound capable of preferentially coupling to the first compound to thereby release the API from the complex.

In another aspect of the present invention, there is provided a method for making an additive for preventing diversion and/or abuse of an active pharmaceutical ingredient (API), comprising the steps of:

obtaining a first compound capable of coupling to an API present in an acidic form to form a complex, said complex being resistant to separation by conventional separation methods;

obtaining a second compound capable of preferentially coupling to the first compound to thereby release the API from the complex; and admixing the first and second compounds together.

BRIEF DESCRIPTION OF THE DRAWINGS

The following drawings are illustrative of embodiments of the present invention and are not intended to limit the invention as encompassed by the claims forming part of the application.

DETAILED DESCRIPTION OF THE INVENTION

Figure 1:
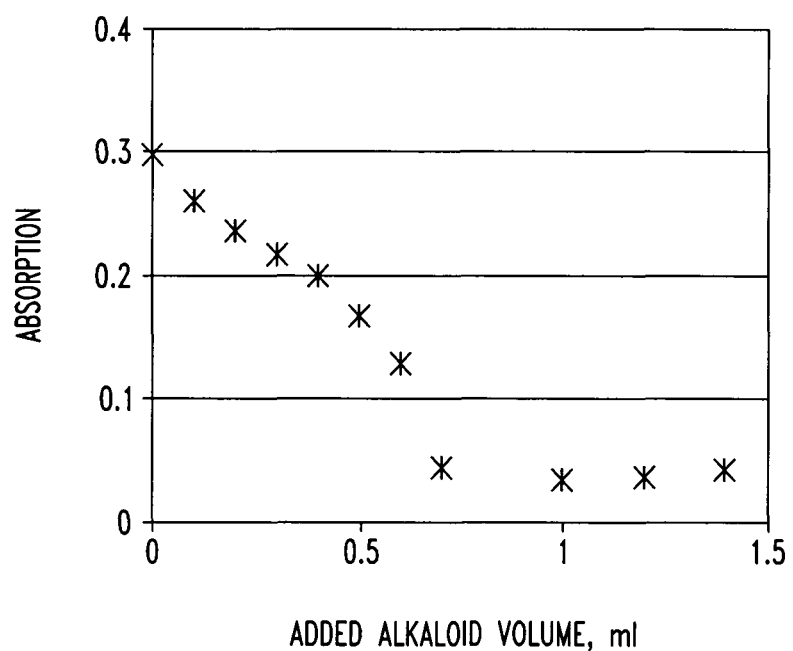
FIG. 1 is a graph illustrating the ultraviolet spectrum absorption of tannins containing solution at 430 nm after addition of a solution containing aminophylline in accordance with the present invention.

The present invention directed generally to a system wherein an active pharmaceutical ingredient (API) can be delivered to a patient for prescribed medical use, but is diversion- and/or abuse-resistant to at least deter illicit use of the API. More specifically, there is provided in accordance with the present invention a pharmaceutical composition containing an API and an additive, which prevents effective separation of the API by conventional separation techniques and/or prevents the administration of the API for a non-therapeutic or non-medical effect (e.g., recreational abuse). Methods of formulating the API-containing compositions and their use in delivering the API for prescribed medical use are also within the scope of the present invention.

In the world of drug abuse, illicit users have available relatively simple chemical and physical separation techniques as mentioned above. The present invention at least deters use of these simple chemical and physical separation techniques and thereby renders it very difficult if not impossible for illicit users to divert and/or abuse the API.

The composition of the present invention is specifically formulated to release the API under conditions of intended use. In particular, the present invention provides a novel combination of an API present in an acidic form with certain components or ingredients that together exhibit a unique set of chemical and physical properties useful for rendering the resulting composition diversion- and/or abuse-resistant. The compositions of the present invention including pharmaceutical compositions derived therefrom, include at least one API, each present in an acidic form.

The composition of the present invention further includes an additive comprising a first compound capable of coupling to the API present in an acidic form to form a complex in which the coupled API is resistant to separation through conventional separation methods, and a second compound capable of preferentially coupling to the first compound to thereby release the API from the complex under conditions of intended use. Preferably, the first compound is further capable of undergoing autooxidation and forming a suspension of fine particles in the presence of the API upon exposure to an increase in the pH (e.g., alkaline pH conditions) useful for enhancing the diversion-resistance of the composition. The composition of the present invention may be formulated into any suitable dosage form including, but not limited to, tablets, soft and hard capsules, gels, liquid or oral solutions, and the like.

As used herein, the term "acidic form of API" refers to any API that is in or has been converted to an acid form with an acid including strong or weak acids. Examples of suitable strong acids are is a strong acid such as hydrochloric acid, sulfuric acid, hydrobromic acid, chloric acid, nitric acid and the like. Examples of suitable weak acids are phosphoric acid, acetic acid, formic acid, tartaric acid, citric acid, succinic acid, oxalic acid, and the like. In a preferred embodiment, the acid used is a strong acid, more preferably hydrochloric acid.

Once the acidic form of the API is complexed with the first compound, the API cannot be separated via any economically-feasible physical or chemical separation method such as by converting the salt form of the drug to the base form and then separating the API with a non-polar solvent. Preferably, the first compound is further capable of undergoing autooxidation and forming a suspension of fine particles in the presence of the API upon exposure to an increase in the pH (e.g., alkaline pH conditions) useful for enhancing the diversion-resistance of the composition of the present invention.

The first compound further preferably exhibits strong astringent properties including the capacity to shrink or constrict body tissues such as blood vessels and mucous membranes in warm-blooded animals including humans. The astringent properties of the first compound facilitate the prevention or deterrence of abusive uses of the present composition (e.g., snorting or overdosing). The constrictive activity induced by the first compound impedes or substantially reduces the absorption of the API under conditions of abuse. In this manner, the astringent properties of the first compound are useful for enhancing the abuse-resistance of the composition of the present invention.

The present invention is applicable for modification of pharmaceutical formulations that contain synthetic, semi-synthetic or naturally or plant-derived API, their analogs or their precursor materials, including, but not limited to, tranquilizers, anti-depression drugs, sleeping disorder drugs, psychotropic drugs, and cold remedies.

In a preferred embodiment of the invention, the first compound is selected from polyphenols. Polyphenols exhibit the ability to complex with the acidic form of the API, the tendency to undergo autooxidation and form a suspension of fine particles in the presence of the API upon exposure to an increase in the pH (e.g., alkaline pH conditions), and strong astringent properties including shrinkage or constriction of body tissue. Such polyphenols include hydrolyzable tannins such as gallic acid esters of sugars, and phenylpropanoids such as lignins, flavonoids, and condensed tannins. Particularly preferred polyphenols include tannic acid and gallic acid. The ability of the polyphenols to bind, precipitate and shrink proteins, makes these compounds effective against abuse, while the tendency to autooxidize at higher pH levels (e.g., alkaline pH conditions) makes them effective against diversion.

The coupling of the polyphenol to the acidic form of the API forms an insoluble complex that reduces the bioavailability of the API, and effectively renders the resulting composition diversion- and/or abuse-resistant. As previously discussed, the insoluble complex is resistant to separation by conventional methods thus making it difficult to isolate the API. To restore the bioavailability of the API, the second compound engages the complex under certain conditions to substitute and release the API. As a result, the API is released from the insoluble complex to perform its intended function.

The tendency for the polyphenol to autooxidize and form a suspension of fine particles in the presence of the API upon exposure to an increase in the pH (e.g., alkaline pH conditions) further renders the composition diversion-resistant. Under conditions of abuse, the ability of the polyphenol to shrink or constrict body tissue including the mucous membranes and blood vessels, significantly reduces the absorption of the API by the body such as through the mucosal membranes or the gastrointestinal lining.

In a preferred embodiment of the present invention, the second compound is a water soluble polymer including, but not limited to, a polyalkyleneoxide such as, for example, polyethylene glycol.

In a preferred embodiment of the present invention, the sum of the amounts of the first compound and the second compound exceed the amount of the API.

In a further preferred embodiment of the present invention, the weight ratio of the API to the first compound to the second compound is in the range of from about 1:1-10:1-30. More preferably, the weight ratio is from about 1:1-3:5-10, and even more preferably about 1:1:7.

The composition of the present invention may further include surfactants such as, for example, polysorbate-80, sodium lauryl sulfate, and the like, and/or gel forming compounds such as, for example, alginic acid, chitosan, collagen, gelatin, sulfated polysaccharides, and the like, as colloid solution stabilizers to further enhance diversion- and/or abuse-resistant properties especially for API such as alkaloids with high molecular weights. The amount of the surfactants and gel forming compounds is a conventional amount typically used in pharmaceutical compositions, such as from about 0.1% to 5.0% by weight based on the total weight of the composition. The amount of surfactant alone may range from about 0.1% to 1.0% by weight based on the total weight of the composition.

The terms "active pharmacological ingredient" or "API" as used herein is intended to refer to any compound capable of inducing a biological, physiological or pharmacological response (e.g., hallucinogenic effects) in warm-blooded animals including humans, possessing the potential for illicit use including, but not limited to, misappropriation, drug abuse, diversion, and the like, and capable of forming a complex with the first compound (e.g., polyphenols) under certain conditions. In addition, API includes compounds, which offer potential for profit in the illicit drug market without regard to whether or not there is the potential for abuse. Accordingly, the present invention encompasses any API that may be desirable for extraction, isolation, or separation from a composition, formulation or mixture for purposes beyond its intended use or application.

Non-limiting illustrative examples of specific active pharmaceutical ingredients (API) utilized in the present invention are ephedrine, pseudoephedrine, opiates (morphine, oxycodone, codeine), trimeperidine (promedol), prodine, atropine, hyosyamine, platyphilline, relanium, seduxen, phenazepam, oxazepam, diazepam, tisercin, barbiturates, oxybutyrate, aminazine, and the like.

In a preferred embodiment of the present invention, the API is selected from an alkaloid. The composition of the present invention may be specifically formulated to release the alkaloid under conditions of intended use.

As used herein, the term "alkaloid" is intended to refer to any chemical compound or a precursor thereof, having basic nitrogen atoms or nitrogen-containing base such as an amine, and preferably to those having a pharmacological effect on warm-blooded animals including humans. The alkaloid may be natural, synthetic or semi-synthetic. Included are alkaloids naturally produced by a large variety of organisms, including bacteria, fungi, plants, and animals. The basicity of alkaloids is the result of the lone pairs of electrons on the nitrogen atoms. Alkaloids often have important pharmacological effects and are used as medications and recreational drugs.

Examples of alkaloids include, but are not limited to, ephedrine, pseudoephedrine, phenyl propanol amine, opiates such as oxycodone, morphine, hydrocodone, oxymorphone, and the like.

Alkaloids are also often classified as follows.

The pyridine group includes piperine, coniine, trigonelline, arecoline, arecaidine, guvacine, cytisine, lobeline, nicotine, anabasine, sparteine, pelletierine, and the like.

The pyrrolidine group includes hygrine, cuscohygrine, and nicotine. The tropane group is selected from atropine, cocaine, ecgonine, scopolamine, catuabine, and the like.

The quinoline group includes quinine, quinidine, dihydroquinine, dihydroquinidine, strychnine, brucine, veratrine, cevadine, and the like.

The isoquinoline group includes opium alkaloids (papaverine, narcotine, narceine), sanguinarine, hydrastine, berberine, emetine, berbamine, oxyacanthine, and the like.

The phenanthrene alkaloids include the opium alkaloids, morphine, codeine, thebaine, and the like.

The phenethylamine group includes mescaline, ephedrine, dopamine, and the like.

The indole group includes tryptamines, serotonin, dimethyltryptamine (DMT), 5-MeO-dimethyltryptamine, bufotenine, psilocybin, ergolines, the ergot alkaloids, ergine, ergotamine, lysergic acid, b-carbolines, harmine, harmaline, tetrahydroharmine, Yohimbans, reserpine, yohimbine, vinca alkaloids, vinblastine, vincristine, Mitragyna speciosa alkaloids, mitragynine, 7-hydroxymitragynine, Tabernanthe iboga alkaloids, ibogaine, voacangine, coronaridine, Strychnos nux-vomica alkaloids, strychnine, brucine, and the like.

The purine group includes xanthines, caffeine, theobromine, theophylline, and the like.

The terpenoid group includes aconite alkaloids, aconitine, steroid alkaloids (containing a steroid skeleton in a nitrogen containing structure), solanum (e.g. potato and tomato) alkaloids, solanidine, solanine, chaconine, veratrum alkaloids, veratramine, cyclopamine, cycloposine, jervine, muldamine, newt alkaloids, samandarin, conessine, and the like.

The quaternary ammonium compounds include muscarine, choline, neurine, and the like.

Miscellaneous alkaloids include capsaicin, cynarin, phytolaccine, phytolaccotoxin, and the like.

In a preferred embodiment of the present invention, the alkaloid is an opioid selected from alfentanil, buprenorphine, butorphanol, carfeotanil, cocaine, codeine, dezocioe, diacetylmorphine, dihydrocodeine, dihydromorphine, dipheaoxylate, diprenorphine, etorphine, fentanyl, heroin, hydrocodone, hydromorphone, b-hydroxy-3-methylfentantanyl, levo-a-acetylmethadol, levorphanol, lofentanil, meperidine, methadone, morphine, nalbuphine, nalmefene, o-methylnaltrexone, naloxone, naltrexone, oxycodone, oxymorphoae, pentazocine, pethidine, propoxyphene, remifentanil, sufentanil, tilidine, tramadol, and the like.

More preferably, the opioid is selected from codeine, diacetylmorphine, dihydrocodeine, hydrocodone, hydromorphone, meperidine, methadone, morphine, oxycodone, oxymorphone, and propoxyphene, and combinations thereof.

As used herein, the term "polyphenol" is intended to refer to any natural, synthetic or semi-synthetic compound characterized by the presence of at least one phenol group or unit, and capable of coupling to an acidic form of an API (e.g., alkaloid) to form a complex resistant to separation via conventional separation methods. Preferably, the polyphenol further exhibits astringent properties including binding, precipitating or shrinking of proteins.

The term "astringent" refers to a chemical property of a compound that induces shrinkage or constriction of body tissues such as mucous membranes and blood vessels, usually locally after topical contact. Astringency is also the dry, puckering mouthfeel caused by tannins found in many fruits. The tannins denature the salivary proteins, causing a rough "sandpapery" sensation in the mouth. Astringent compounds cause shrinkage of mucous membranes or exposed tissues and are often used internally to check discharge of blood serum or mucous secretions.

The polyphenol may be selected from tannins including hydrolyzable tannins, phenylpropanoids, compounds having at least one phenolic subcomponent selected from phenols, pyrocatechols, pyrogallols, resorcinol, phloroglucinol, hydroquinone, and the like, and combinations thereof. The phenolic subcomponents may be esterified, methylated, dimerized, or further polymerized. Preferred polyphenols are selected from tannins, tannic acid, gallic acid, and combinations thereof. The most preferred polyphenols are tannins.

Examples of hydrolyzable tannins include, but are not limited to, gallic acid esters of sugars such as glucose.

Examples of phenylpropanoids include, but are not limited to, lignins, flavonoids, and condensed tannins. The flavonoids may be selected from flavonols, flavones, catechins, flavanones, anthocyanidins, isoflavanoids, and combinations thereof.

Tannins are astringent, bitter plant polyphenols that exhibit the capacity to bind, precipitate or shrink proteins. The term "tannins" as used herein refers to any relatively large polyphenolic compound containing sufficient hydroxyls and other suitable groups (e.g., carboxyls) to form strong complexes with proteins and other macromolecules. Tannins typically have molecular weights ranging from about 500 to 3,000.

Hydrolyzable tannins include a carbohydrate (e.g., D-glucose) in the center of the tannins molecule. The hydroxyl groups of the carbohydrate are partially or totally esterified with phenolic groups such as gallic acid (i.e., gallotannins) or ellagic acid (i.e., ellagitannins). Hydrolyzable tannins are hydrolyzed by weak acids or weak bases to produce carbohydrate and phenolic acids. Examples of gallotannins are gallic acid esters of glucose in tannic acid ($C_{76}H_{52}O_{46}$). Condensed tannins also known as proanthocyanidins, include polymers of at least two flavonoid units joined by carbon-carbon bonds.

As used herein, the term "water soluble polymer" is intended to refer to a water soluble hydrophilic compound capable of preferentially coupling to a first compound, preferably a polyphenol, coupled to an API (e.g, alkaloid) in a complex to thereby release the API therefrom.

Examples of water soluble polymers include, but are not limited to, polyalkyleneoxides, polyvinyl pyrrolidone, and the like.

Preferred water soluble polymers are selected from polyalkyleneoxides, water soluble polymers linked with polyalkyleneoxide chains, and combinations thereof.

Examples of polyalkyleneoxides include, but are not limited to, polyethyleneoxide, polypropyleneoxide, polyethylene glycol, and the like. Preferably, the water soluble polymer is polyethylene glycol. The molecular weight of the water soluble polymer is preferably at least 400 Da, and more preferably in the range of from about 400 Da to 40,000 Da.

As used herein, the term "therapeutic purpose" is intended to refer broadly to any medically-appropriate treatment, alleviation, prevention or relief from a condition, disease or symptom in a warm-blooded animal.

As used herein, the term "therapeutically effective amount" is intended to refer to an amount of an API (e.g., alkaloid) whether by single dosage or a dosage regimen that elicits a desirable biological or pharmacological response in a tissue or system of a warm-blooded animal to achieve a therapeutic purpose.

The term "pharmaceutically acceptable," such as pharmaceutically acceptable carrier, excipient, and the like, means a compound, which is pharmacologically acceptable and substantially non-toxic to the patient.

The first compounds of the present invention including polyphenols such as, for example, tannins, tannic acid, and gallic acid, exhibit a strong binding or coupling affinity with an API to form a complex, and are exceptionally difficult to separate from the API. The formation of the complex significantly reduces or limits the bioavailability of the API. The resulting composition is rendered diversion-resistant. The presence of the second compounds of the present invention including water soluble polymers such as, for example, polyalkyleneoxides, releases the API (e.g., alkaloid) from the polyphenol-API complex under certain conditions, and restores the bioavailability of the API (e.g., alkaloid).

Polyphenols further exhibit astringent properties useful for rendering the present compositions abuse-resistant. Concentrations of the polyphenols above a certain threshold results in severe constriction of body tissues including blood vessels, mucous membranes and gastrointestinal linings, which significantly reduces the capacity of the body to absorb the API (e.g., alkaloid). Accordingly, as the concentration of polyphenols increases, such as during conditions of abuse or overdose, the body's capacity to take up the API (e.g., alkaloid) becomes more severely compromised.

When administered orally, the components of the present composition are released in the stomach. The first and second compounds (e.g., polyphenol and water soluble polymer, respectively) normally form with one another an insoluble complex, thus restoring the bioavailability of the API (e.g., alkaloid). Small quantities of the polyphenol and the water soluble polymer remain in the stomach in an equilibrium state as the API (e.g., alkaloid) is absorbed through the gastrointestinal lining.

If the present composition is administered through snorting or overdosing, the astringent properties of the polyphenol cause the blood vessels in the mucous membranes or gastrointestinal lining to shrink and impede or inhibit the uptake of the API (e.g., alkaloid) into the body. As the concentration of the polyphenol increases further (e.g., due to abuse with larger dosage amounts), the corresponding constricting effect on the body tissue (e.g., blood vessels) becomes more pronounced, thus further inhibiting uptake of the API (e.g., alkaloid) and deterring or thwarting further abusive use of the API (e.g., alkaloid).

The presence of the additive comprising the first and second compounds makes any attempts to separate the API (e.g., alkaloid) from the composition of the present invention, exceedingly difficult using conventional separation methods. When dissolved in acidic or slightly basic solutions, the first and second compounds couple to yield an insoluble complex in the form of a suspension of fine particles. The fine suspension can only be separated through the use of modern, expensive and not readily attainable devices or techniques such as, for example, ultrafiltration or preparatory chromatography. In the event that the fine suspension can be removed, a significant quantity of dissolved first and second compounds remains thereby preventing or hindering separation of the API (e.g., alkaloid). The separation process becomes increasingly difficult with each finished form.

When the pH is raised in an attempt to precipitate the API (e.g., alkaloid) in base form in preparation for follow-up separation with non-polar solvent, the first compound (e.g., polyphenol) undergoes auto-oxidation to yield a suspension of fine particles with the API (e.g., alkaloid) in a finely dispersed form. The subsequent use of the non-polar solvent forms a stable viscous emulsion due to the relatively large concentration of the second compound (e.g., water soluble polymer). When a polar solvent is used to dissolve the API (e.g., alkaloid) for parentheral administration, the presence of the second compound causes a severe pyrogenic effect that deters further abuse.

The present invention is further directed to a pharmaceutical composition for administration to a warm-blooded animal for release of an API for a therapeutic purpose, comprising a therapeutically effective amount of at least one API, a first compound capable of coupling to the API to form a complex, where the complex is resistant to separation by conventional separation methods, a second compound capable of preferentially coupling to the first compound within the warm-blooded animal to thereby release the API from the complex, and a pharmaceutical carrier. Optionally, the pharmaceutical composition may further include other therapeutic ingredients.

Pharmaceutical compositions suitable for any route of administration are encompassed by the present invention. Oral administration is the preferred route of administration. Pharmaceutical compositions suitable for oral administration include pills, tablets, troches, soft- and hard-gel capsules, gels, and liquid formulations including dispersions, suspensions, emulsions and solutions. The pharmaceutical compositions may be formulated in unit dosage form and prepared by any method or technique as known in the pharmaceutical arts. Preferred unit dosage formulations are those containing a therapeutically effective amount, or an appropriate fraction thereof, of the API.

The pharmaceutical composition of the present invention further includes a pharmaceutically acceptable carrier. The pharmaceutically acceptable carrier may take a wide variety of forms, depending on the route desired for administration such as, for example, oral administration. In preparing the pharmaceutical composition for oral dosage form, any of the usual pharmaceutically acceptable carriers may be employed, such as, water, glycols, oils, alcohols, flavoring agents, preservatives, and coloring agents in the case of oral liquid preparation, including suspension, elixirs and solutions.

Pharmaceutically acceptable carriers such as starches, sugars, microcrystalline cellulose, diluents, granulating agents, lubricants, binders and disintegrating agents may be used to prepare solid preparations for oral administration such as powders, capsules and caplets, with the solid oral preparations being preferred over the liquid preparations. Preferred solid oral preparations are tablets or capsules, because of their ease of administration. If desired, tablets may be coated by standard aqueous or non-aqueous techniques. Oral sustained release dosage forms may also be used.

Oral syrups, as well as other oral liquid formulations, are well known to those skilled in the art, and general methods for preparing them are found in any standard pharmacy school textbook, for example Remington: The Science and Practice of Pharmacy. Chapter 86 of the 19th edition of Remington entitled "Solutions, Emulsions, Suspensions and Extracts" describes in complete detail the preparation of syrups (pages 1503-1505) and other oral liquids.

Similarly, sustained release formulations are well known in the art, and Chapter 94 of the same reference, entitled "Sustained-Release Drug Delivery Systems," describes the more common types of oral and other sustained-release dosage forms (pages 1660-1675). The relevant disclosure of each of these chapters is incorporated herein by reference. Because they reduce peak plasma concentrations, as compared to conventional oral dosage forms, controlled release dosage forms are particularly useful for providing therapeutic plasma concentrations while avoiding the side effects associated with high peak plasma concentrations that occur with conventional dosage forms.

In an illustrative non-limiting method of the present invention, a solution of an alkaloid (e.g., 2.4% aminophylline) can be slowly added to an aqueous solution of a polyphenol (e.g., tannic acid) in a strong acid (e.g., 0.1 M HCl). A white insoluble precipitate forms, which is removed by filtration to provide the insoluble aminophylline-polyphenol complex. The resulting complex is not a salt produced by the reaction of an alkaloid in basic form with tannic acid. The complex comprises an alkaloid present in an acidic form, for example, in the presence of a strong acid (e.g., HCl). Tannic acid is a much weaker acid than HCl and will not displace HCl in the alkaloid. Reaction of tannic acid with alkaloids is a common reaction of precipitation, which is used, in a chemical analysis. This reaction requires a strong acidic media (pH less than 2). A higher pH does not permit this reaction. Therefore the complex of tannic acid with the alkaloid in the HCl form is not a simple salt formation. Low pH does not allow carboxyl groups of tannic acid to exist in acidic form. Formation of an ionic bond of secondary amino groups of alkaloids with carboxyl groups of tannic acid is not possible under these conditions.

The compositions of the present invention can be prepared according to the examples set out below. The examples are presented for purposes of demonstrating, but not limiting, the preparation of the compounds and compositions of this invention. The components of the present invention including the alkaloids presented in the examples are selected to demonstrate the operability of the present invention, and that such selections are not intended to limit the scope of the present invention.

EXAMPLES

Example 1

General Procedure for the Preparation of an Insoluble Alkaloid-Polyphenol Complex To demonstrate the interaction between a polyphenol such as tannic acid and an alkaloid such as aminophylline in the environment similar to that of the stomach, a 3% wt. tannic acid solution was prepared in 0.1 M HCl. A solution containing an alkaloid (2.4% aminophylline) was slowly added to 3.0 ml of the tannic acid solution in increments of 0.1 ml, 0.2 ml, 0.3 ml, 0.4 ml, 0.5 ml, 0.6 ml, 0.7 ml, 1.0 ml, 1.2 ml and 1.4 ml. After each addition, a white insoluble precipitate was formed, which was then removed from the solution using a 0.2 micron filter. The filtrate, which is a clear solution of a pale-yellow color typical for tannic acid with an intensity inversely proportional to the incremental addition of aminophylline, was then analyzed for tannic acid using UV spectroscopy at a wavelength of 430 nm. The results are shown in FIG. 1. Above a certain dose of alkaloid, no tannic acid was observed to be present in the solution. The data confirms the chemical bonding between tannic acid and aminophylline and the resulting formation of an insoluble aminophylline-tannic acid complex.

Example 2

Release of an Alkaloid with a Water Soluble Polymer from the Alkaloid-Polyphenol Complex An alkaloid-polyphenol complex was prepared in a manner similar to the procedure described in the Example 1. The alkaloid used was drotaverine and the polyphenol used was tannic acid. The resulting precipitate was collected, rinsed with 0.1M HCl, dried at 40° C. for 72 hours and then homogenized. 200 mg of the drotaverine-tannic acid complex were added to 5 ml of 0.1 M HCl solution and mixed. The complex remained insoluble in the resulting solution.

4 ml of a solution containing 10% wt. polyethylene glycol (PEG), with a molecular weight of about 4,000 Da was added under continuous mixing. The drotaverine-tannic acid complex dissolved in the presence of PEG. The resulting solution was filtered through a media filter with a pore diameter of 0.2 µm. The filtrate was then diluted with water by a factor of 150 and analyzed using a UV spectrophotometer in the wavelength range of from about 190 nm to 500 nm.

Figure 2:
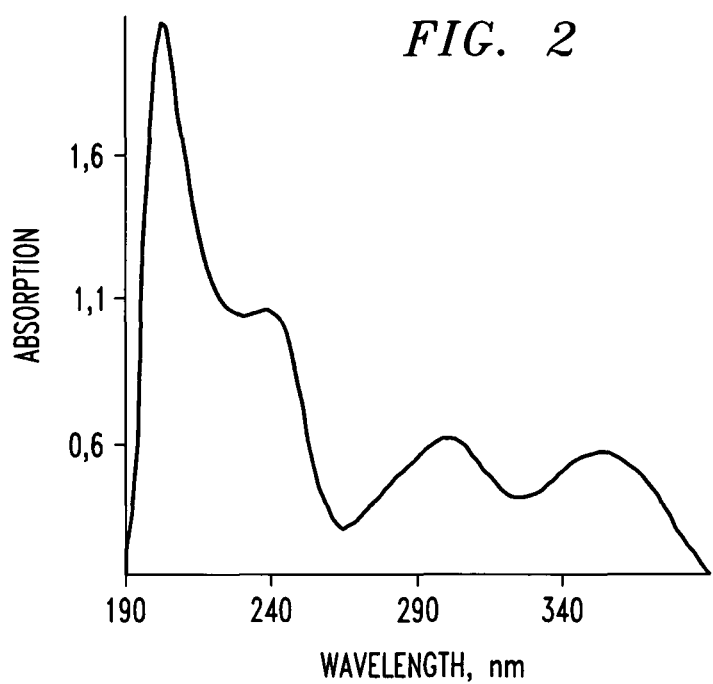
FIG. 2 is a graph illustrating the ultraviolet spectrum absorption of a solution after dissolution of a drotaverine-tannins complex in 0.1M HCl containing 4.4% wt. polyethylene glycol in accordance with the present invention.
Figure 3:
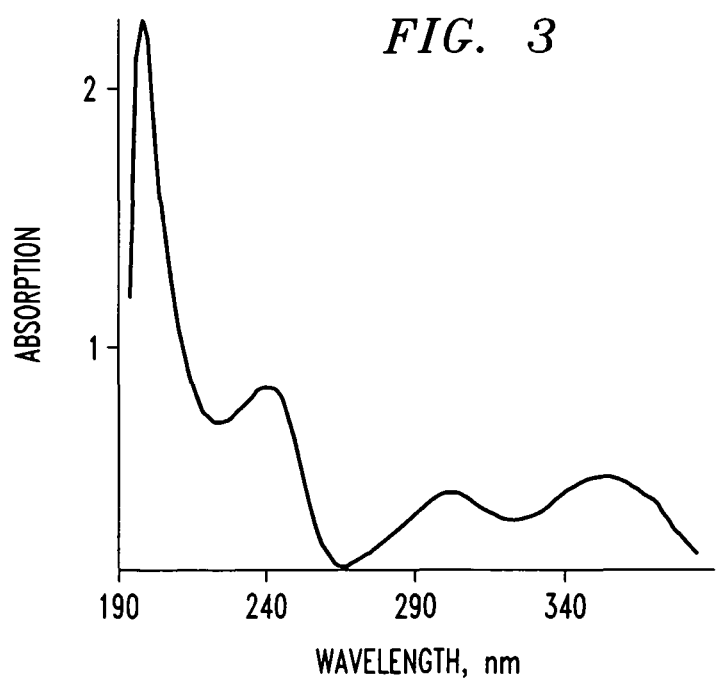
FIG. 3 is a graph illustrating the ultraviolet spectrum absorption of drotaverine in 0.1M HCl in accordance with the present invention.

The UV spectra of the filtrate and the drotaverine standard are shown in FIGS. 2 and 3, respectively. As shown in FIG. 2, the peaks and dips of the UV spectrum of the filtrate, closely matched the UV spectrum of the drovaterine standard in FIG. 3. This confirms that drotaverine was released into the solution from the drotaverine-tannic acid complex upon the addition of polyethylene glycol.

Example 3

Preparation of a Diversion- and/or Abuse-Resistant Alkaloid-Polyphenol Complex

Papaverine HCl, an opium alkaloid used primarily in the treatment of visceral spasm, vasospasm (especially those involving the heart and the brain), and occasionally in the treatment of erectile dysfunction, was selected as a model alkaloid for use in the preparation of the present composition exhibiting diversion- and/or abuse-resistant properties. 100 ml of 2% wt. of papaverine HCl solution was mixed with predetermined volumes of 10% wt. tannic acid solution and 15% wt. PEG solution to yield a papaverine HCL/tannic acid/PEG weight ratio of about 1.0:1.0:15.5.

The resulting solution was mixed for about 20 minutes and then dried at 50° C. in a thermostat for about 60 hours to yield papaverine/tannic acid/PEG in dry form. The papaverine/tannic acid/PEG was homogenized to produce a novel modified papaverine HCL API of the present invention with diversion- and/or abuse-resistant properties. The components of the present composition and respective amounts are listed below in Table 1.

TABLE 1

| Ingredient: | Amount (g): |
| --- | --- |
| Papaverine HCl | 2.0 |
| Tannic acid | 2.0 |
| PEG | 30.0 |

Through traditional tablet formulation and preparation techniques, the papaverine/tannic acid/PEG was formulated into tablets each weighing about 0.4 g utilizing conventional pharmaceutical excipients such as cellulose, silicon dioxide, talc, starch and the like, including 0.5% wt (dry basis) of each of polysorbate-80 and sodium lauryl sulfate (SDS).

One tablet containing a composition of the present invention in the form of papaverine/tannic acid/PEG was placed in 100 ml of 0.1M HCl solution. The dissolution of the tablet was investigated under conditions similar to the environment in the stomach. Samples of the solution were taken at time intervals of 1 minute, 3 minutes, 5 minutes, 7 minutes, 9 minutes, 11 minutes, 13 minutes, 15 minutes, 17 minutes, and 19 minutes after complete dissolution of the tablet. The dissolution time of the present composition containing the modified papaverine was observed to be consistent with the dissolution times required for oral finished forms.

Figure 4:
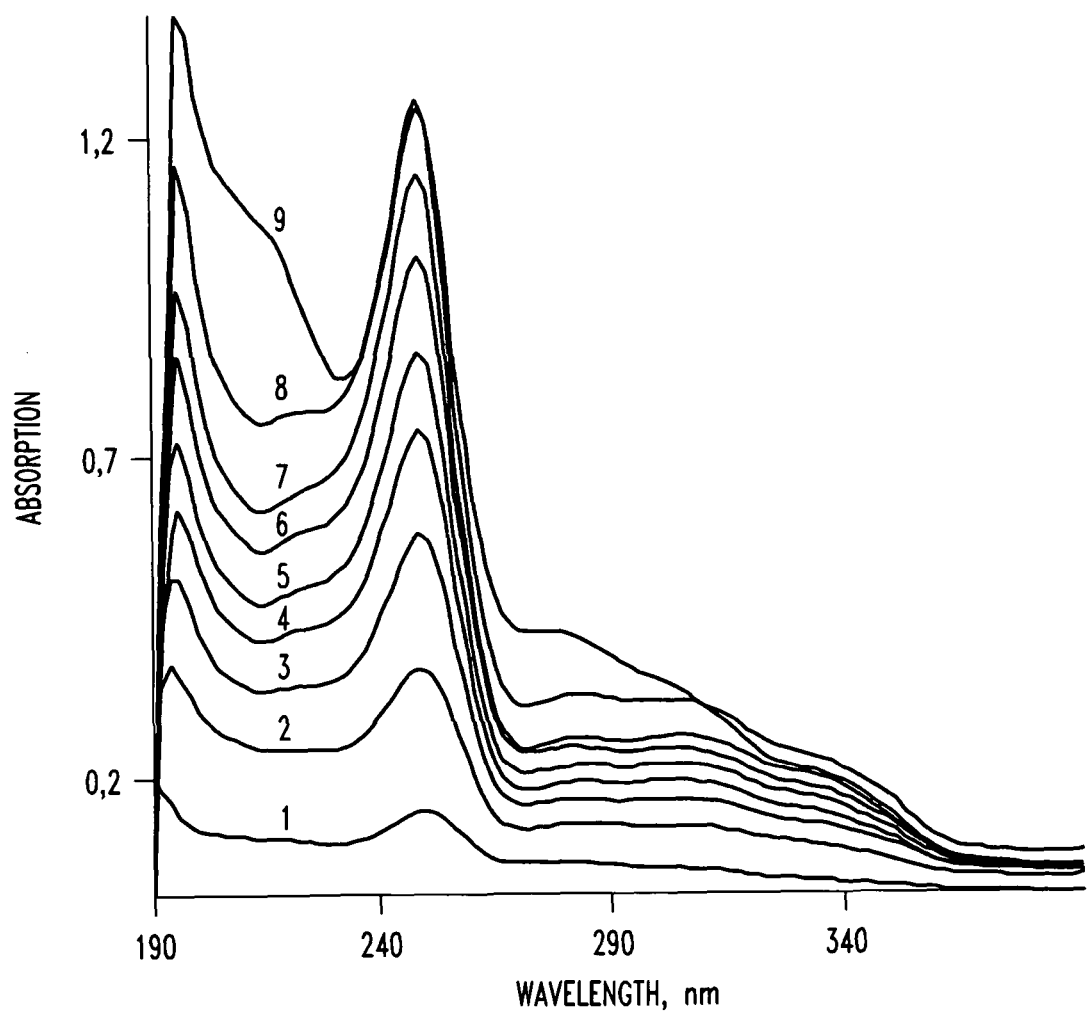
FIG. 4 is a graph illustrating the ultraviolet spectrum absorption of papaverine-tannin-polyethylene glycol complex in 0.1M HCl, whereby the spectrum is shown after (1) 1 minute, (2) 3 minutes, (3) 5 minutes, (4) 7 minutes, (5) 9 minutes, (6) 11 minutes, (7) 13 minutes, (8) 15 minutes, and (9) 17 minutes in accordance with the present invention.
Figure 5:
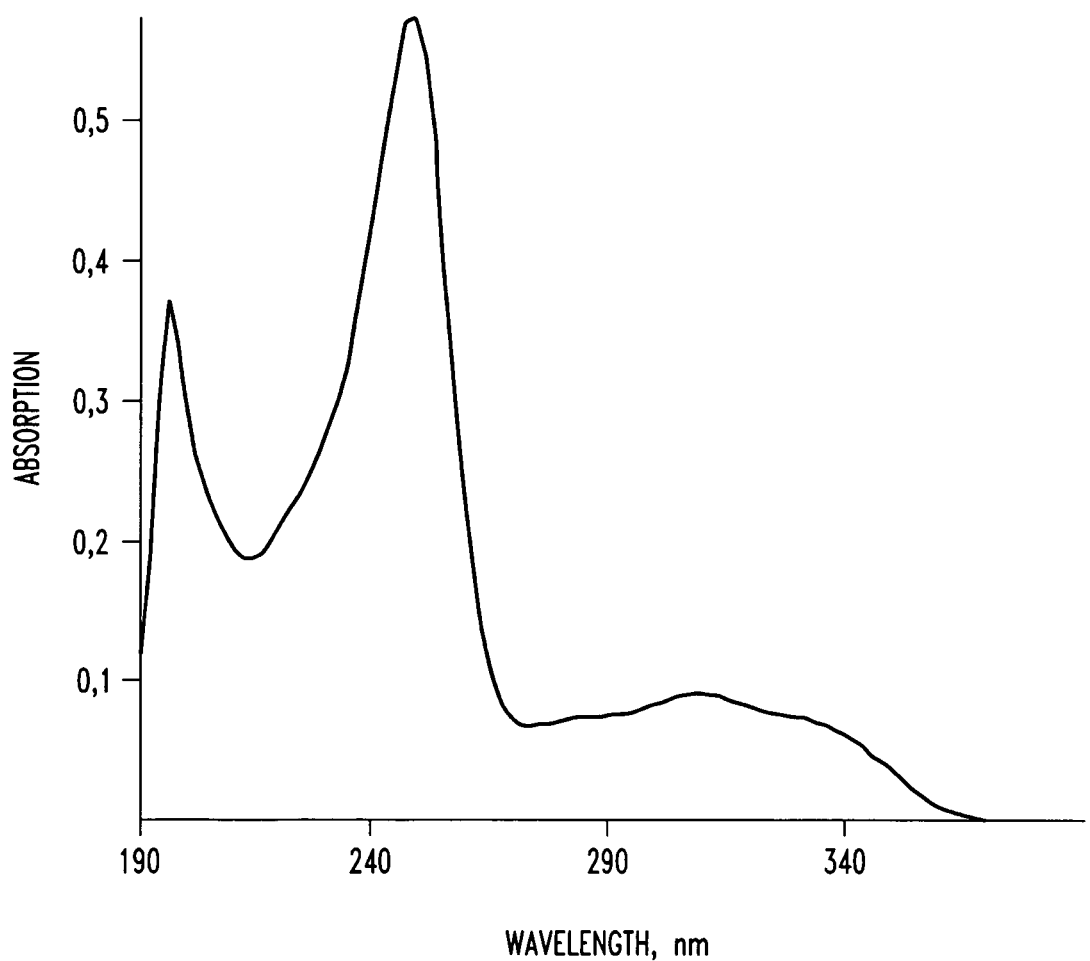
FIG. 5 is a graph illustrating the ultraviolet spectrum absorption of papaverine in 0.1 M HCl in accordance with the present invention.

The solution samples were analyzed using a UV spectrophotometer and compared with a UV spectrum of the pure alkaloid (i.e., papaverine) in 0.1 M HCl solution. The UV spectra of the tablet dissolution and the papaverine standard are shown in FIGS. 4 and 5, respectively. As shown in FIG. 4, the peaks and dips of the UV spectrum of the solution containing the dissolved tablet match the UV spectrum of the papaverine standard in FIG. 5 with each successive sample, thus indicating greater release of papaverine over time. The comparison of the UV spectra shows the full release of papaverine from the papaverine/tannic acid/PEG into the solution.

Example 4

Preparation of a Diversion- and/or Abuse-Resistant Alkaloid-Polyphenol Complex

Aminophylline, a bronchodilator drug combination that contains the alkaloid theophylline, and ethylenediamine in 2:1 ratio, was selected as a model alkaloid for use in the preparation of the present compositions exhibiting diversion- and/or abuse-resistant properties. 100 ml of 2.4% wt. aminophylline aqueous solution was mixed with predetermined volumes of 13% wt. tannic acid aqueous solution and 20% wt. PEG aqueous solution to yield an aminophylline/tannic acid/PEG weight ratio of about 1.0:1.0:7.0.

The resulting solution was mixed for about 20 minutes and then dried at 60° C. in a thermostat for about 60 hours to yield aminophylline/tannic acid/PEG in dry form. The aminophylline/tannic acid/PEG was homogenized to produce a novel modified aminophylline API of the present invention with diversion- and/or abuse-resistant properties. The components of the composition and respective amounts are listed below in Table 2.

TABLE 2

| Ingredient: | Amount (g): |
| --- | --- |
| Aminophylline | 2.4 |
| Tannic acid | 2.4 |
| PEG | 16.8 |

Through traditional tablet formulation and preparation techniques, the aminophylline/tannic acid/PEG was formulated into tablets each weighing about 0.4 g utilizing conventional pharmaceutical excipients such as cellulose, silicon dioxide, talc, starch and the like, including 0.5% wt (dry basis) of each of polysorbate-80 and sodium lauryl sulfate (SDS).

One tablet containing a composition of the present invention in the form of the aminophylline/tannic acid/PEG was placed in 100 ml of 0.1M HCl solution. The dissolution of the tablet was investigated under conditions similar to the environment in the stomach. Samples of the solution were taken at time intervals of 1 minute, 3 minutes, 5 minutes, 7 minutes, 9 minutes, 11 minutes, 13 minutes, 15 minutes, 17 minutes, and 19 minutes after complete dissolution of the tablet. The dissolution time of the present composition containing the modified aminophylline was observed to be consistent with the dissolution times required for oral finished forms.

Figure 6:
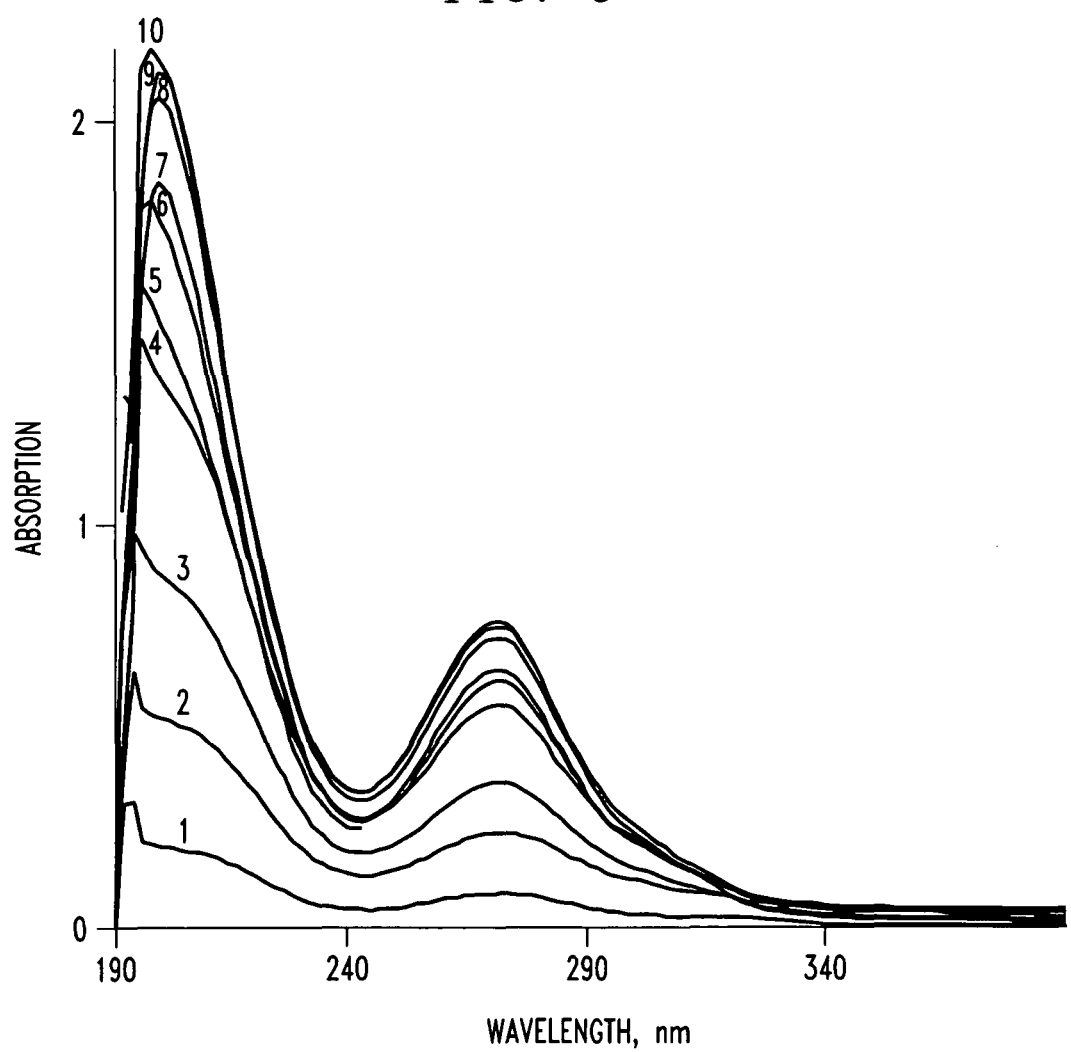
FIG. 6 is a graph illustrating the ultraviolet spectrum absorption of an aminophylline-tannin-polyethylene glycol complex in 0.1M HCl, whereby the spectrum is shown after (1) 1 minute, (2) 3 minutes, (3) 5 minutes, (4) 7 minutes, (5) 9 minutes, (6) 11 minutes, (7) 13 minutes, (8) 15 minutes, (9) 17 minutes, and (10) 19 min in accordance with the present invention.
Figure 7:
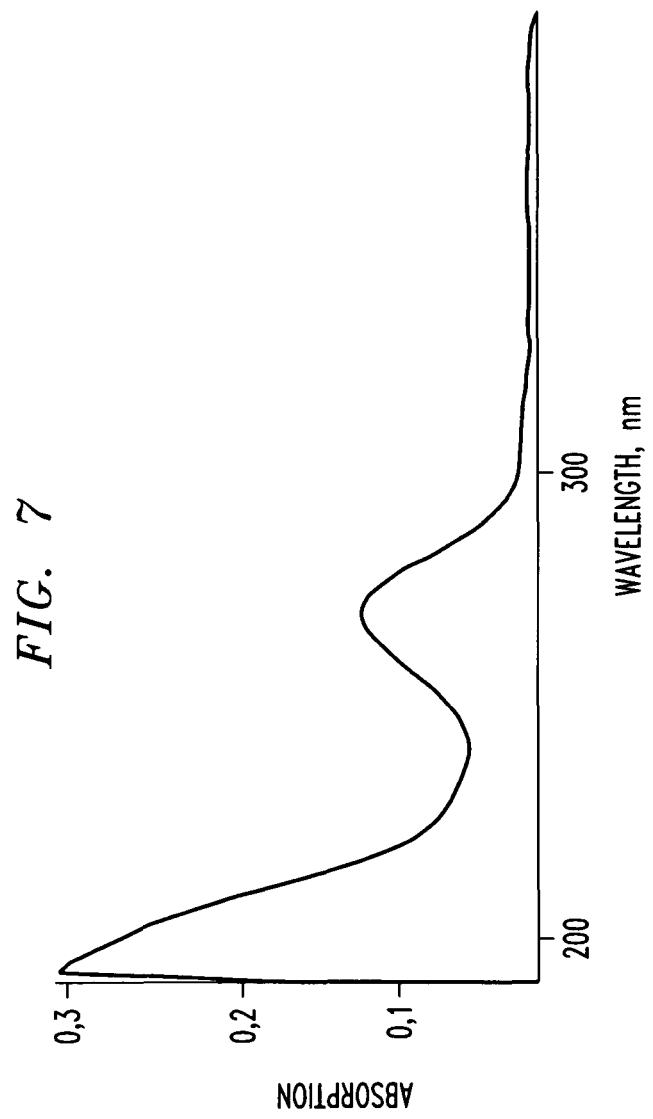
FIG. 7 is a graph illustrating the ultraviolet spectrum absorption of aminophylline in 0.1 M HCl in accordance with the present invention.

The solution samples were analyzed using a UV spectrophotometer and compared with a UV spectrum of the pure alkaloid (i.e., aminophylline) in 0.1 M HCl solution. The UV spectra of the tablet dissolution and the aminophylline standard are shown in FIGS. 6 and 7, respectively. As shown in FIG. 6, the peaks and dips of the UV spectrum of the solution containing the dissolved tablet matched the UV spectrum of the aminophylline standard in FIG. 7 with each successive sample, thus indicating greater release of aminophylline over time. The comparison of the UV spectra shows the full release of aminophylline from the papaverine/tannic acid/PEG mixture into the solution.

Example 5

Preparation of a Diversion- and/or Abuse-Resistant Alkaloid-Polyphenol Complex Drotaverine HCl, an antispasmodic alkaloid structurally related to papaverine, was selected as a model alkaloid for use in the preparation of the present compositions exhibiting diversion- and/or abuse-resistant properties. 20 ml of 2.0% wt. drotaverine aqueous solution was mixed with predetermined volumes of 26% wt. tannic acid aqueous solution and 20% wt. PEG aqueous solution to yield a mixture of drotaverine/tannic acid/PEG in a weight ratio of 1:10:30.

The resulting solution was mixed for about 10 minutes and then dried at 40° C. in a thermostat for about 72 hours to yield the drotaverine/tannic acid/PEG in dry form. The drotaverine/tannic acid/PEG was homogenized to produce a novel modified drotaverine HCl API of the present invention with diversion- and/or abuse-resistant properties. The components of the composition and respective amounts are listed below in Table 3.

TABLE 3

| Ingredient: | Amount (g): |
|---|---|
| Drotaverine | 0.4 |
| Tannic acid | 4.0 |
| PEG | 12.0 |

Through traditional tablet formulation and preparation techniques, the drotaverine/tannic acid/PEG was formulated into tablets each weighing about 0.4 g utilizing conventional pharmaceutical excipients such as cellulose, silicon dioxide, talc, starch and the like, including 0.5% wt (dry basis) of each of polysorbate-80 and sodium lauryl sulfate (SDS).

One tablet containing a composition of the present invention in the form of the drotaverine/tannic acid/PEG was placed in 100 ml of 0.1M HCl solution. The dissolution of the tablet was investigated under conditions similar to the environment in the stomach. Samples of the solution were taken at time intervals of 1 minute, 3 minutes, 5 minutes, 7 minutes, 9 minutes, 11 minutes, 13 minutes, 15 minutes, 17 minutes, and 19 minutes after complete dissolution of the tablet. The dissolution time of the present composition containing the modified drotaverine was observed to be consistent with the dissolution times required for oral finished forms.

Figure 8:
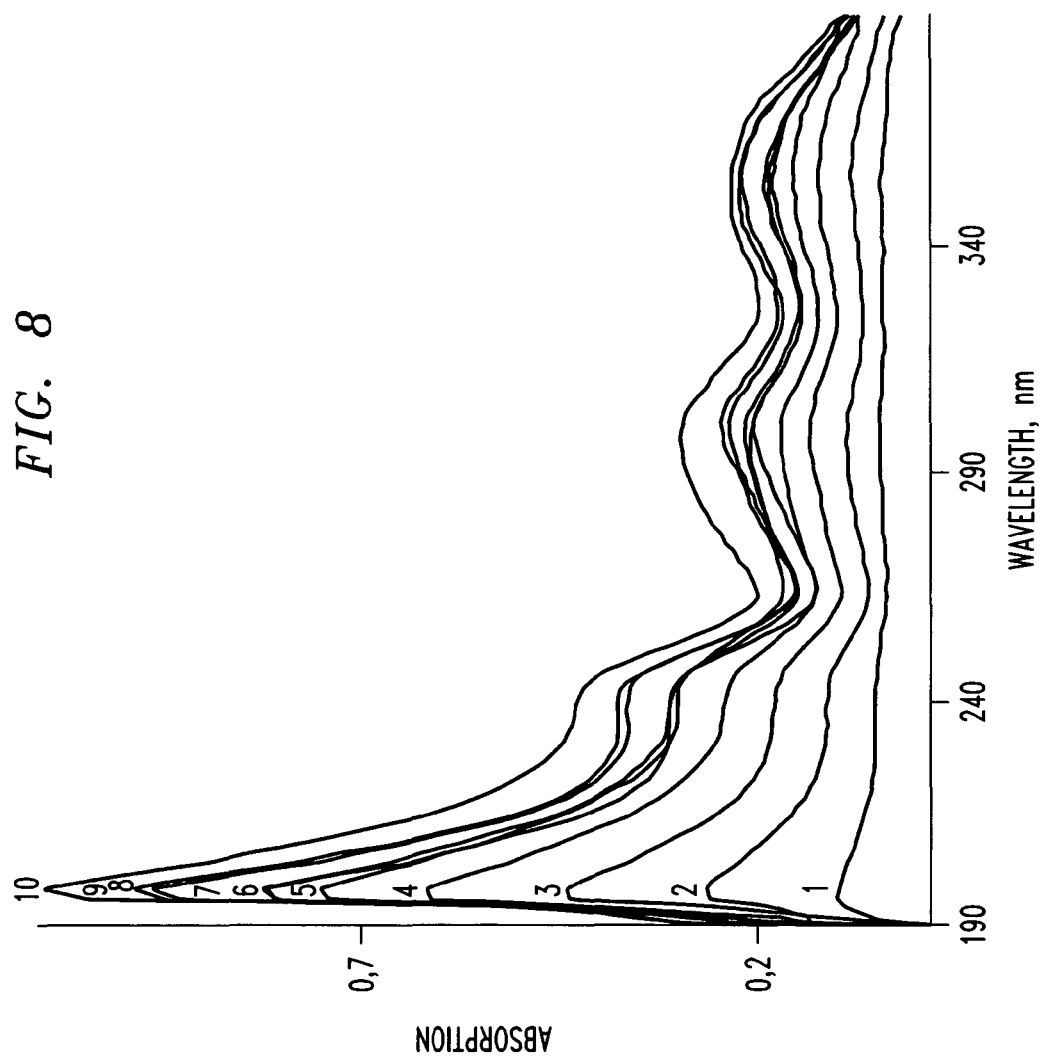
FIG. 8 is a graph illustrating the ultraviolet spectrum absorption of a drotaverine-tannin-polyethylene glycol complex in 0.1M HCl, whereby the spectrum is shown after (1) 1 minute, (2) 3 minutes, (3) 5 minutes, (4) 7 minutes, (5) 9 minutes, (6) 11 minutes, (7) 13 minutes, (8) 15 minutes, (9) 17 minutes, and (10) 19 minutes in accordance with the present invention.

The solution samples were analyzed using a UV spectrophotometer and compared with a UV spectrum of pure alkaloid (i.e., drotaverine) in 0.1 M HCl solution. The UV spectra of the tablet dissolution and the drotaverine standard are shown in FIGS. 8 and 3, respectively. As shown in FIG. 8, the peaks and dips of the UV spectrum of the solution containing the dissolved tablet matched the UV spectrum of the drotaverine standard in FIG. 3 with each successive sample, thus indicating greater release of drotaverine over time. The comparison of the UV spectra shows the full release of drotaverine from the drotaverine/tannic aid/PEG into the solution.

Example 6

Verification of Diversion-Resistant Properties of the Present Compositions

To demonstrate diversion-resistant properties of the present compositions containing an alkaloid, tablets prepared in Examples 3 through 5 were subjected to typical diversion methods such as dissolution in a polar solvent such as ethanol, followed by increasing the pH through the addition of caustic soda, and extraction with a polar solvent such as xylene. The results are shown below in the Table 4.

TABLE 4

| Modified API | Addition of ethanol | Addition of caustic soda to ethanol | Addition of xylene to basic ethanol, mixing |
|---|---|---|---|
| 1) Papaverine HCl | Complete dissolution, clear yellow-pale solution | Solution turns brown-red with fine suspension-product of tannic acid auto-oxidation | True emulsion is formed, no phase separation |
| 2) Aminophylline* | Complete dissolution, clear light yellow solution | Solution turns brown-red with fine suspension-product of tannic acid auto-oxidation | True emulsion is formed, no phase separation |
| 3) Drotaverine HCl | Complete dissolution, clear green-pale solution | Solution turns brown-red with fine suspension-product of tannic acid auto-oxidation | True emulsion is formed, no phase separation |

*Aminophylline is composed of a combination of theophylline and ethylenediamine, each present in an acidic form.

The use of traditional diversion techniques or conventional separation methods typically results in solutions, fine suspensions or emulsions that cannot be easily treated to remove the alkaloid. As shown specifically in Table 4, the attempts at separation of the API resulted in the formation of an undesirable emulsion, evidencing no phase separation and no isolation of the API.

Example 7

Verification of Abuse-Resistant Properties of the Present Compositions Against Recreational Abuse Through Nasal Inhalation To demonstrate the abuse-resistant properties of the present composition, various aminophylline-based solutions as listed below in Table 5, were prepared and intranasally administered to male mice (CBA C50 Black F1 line), each having an average weight of from about 30 g to 40 g.

TABLE 5

| | Concentration in aqueous solution (% Wt) | | Weight Ratio of Components in the Abuse-Resistant Formulation | | |
|---|---|---|---|---|---|
| Sample ID | Aminophylline | Total | Aminophylline | Polyethylene Glycol (MW 4000 Da) | Tannin |
| Control-1 | 4.0 | 4.0 | — | — | — |
| Control-2 | 24 | 24 | — | — | — |
| Formulation 1 | 4.0 | 50 | 10.5 | 79.0 | 10.5 |
| Formulation 2 | 4.0 | 50 | 9.5 | 71.5 | 19.0 |
| Formulation 3 | 4.0 | 50 | 8.7 | 65.2 | 26.1 |
| Formulation 4 | 2.0 | 25 | 9.5 | 71.5 | 19.0 |

10 µL of each experimental solution was administered to a corresponding pool of three mice. About 3 to 5 minutes after administration, blood samples were drawn from the retro-orbital sinuses (sinus retroorbitalis) of the mice, combined and centrifuged for 10 minutes at 3000 rpm. The collected serum was then deproteinized with 0.3 M trichloroacetic acid at a serum to acid ratio of about 0.2 ml to 1.0 ml. To complete the precipitation of proteins, the samples were maintained in a thermostat at 20° C. for about 20 minutes and then filtered through a 0.45 micron acetate cellulose filter. The filtrates were analyzed for aminophylline concentration by injecting 20 µL samples into an HPLC, Schimadzu LC-20AD with photodiode array detector (PDA) and Phenomenex Luna 5µ C18, 250×460 mm column. Acetonitrile in 0.1M phosphoric acid was used as a Mobile phase with linear gradient of acetonitrile of 1-50% vol., pressure 6.3 Mpa, flow rate 0.5 ml/min, and detector wavelength of about 272 nm.

Figure 9:
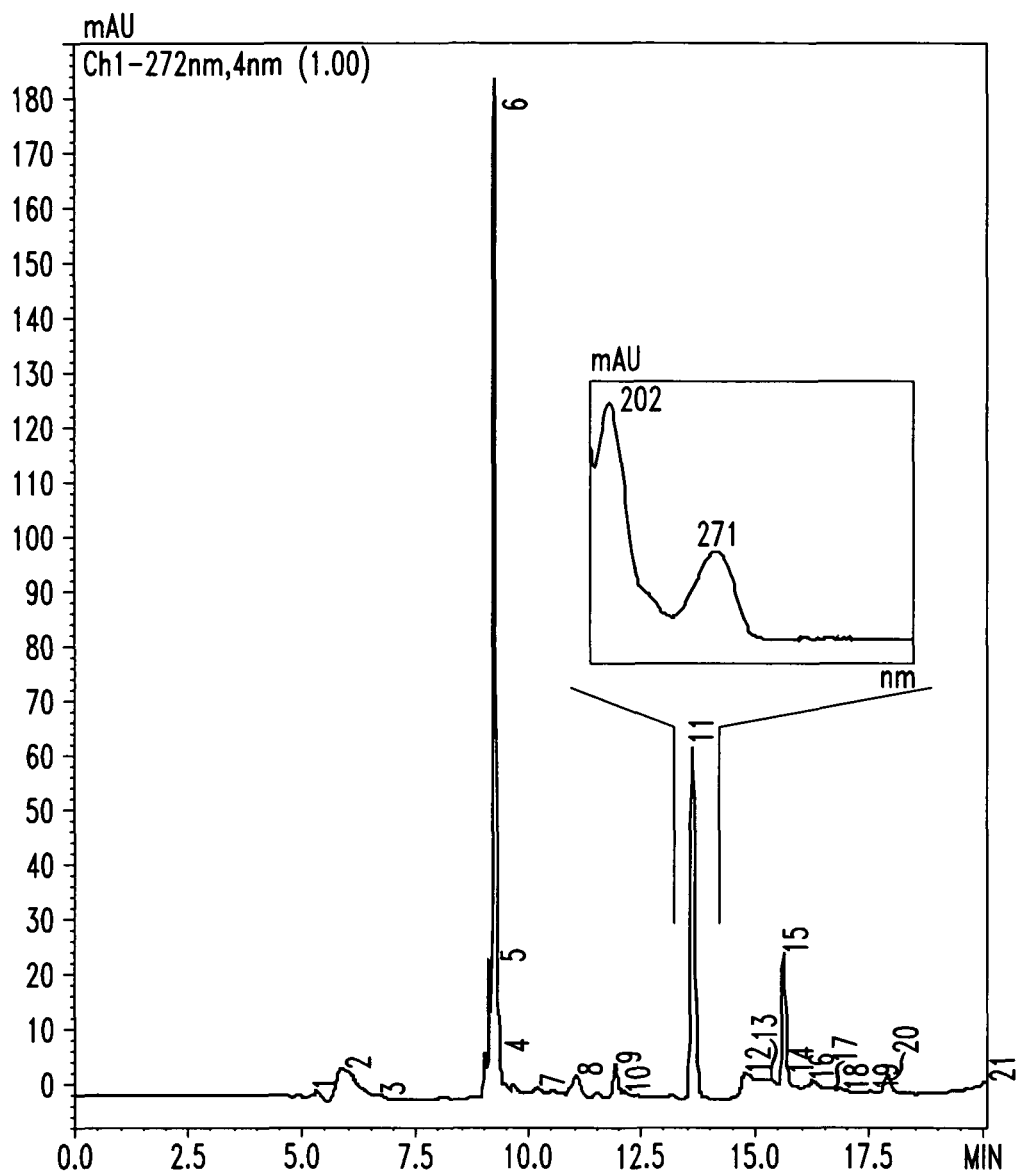
FIG. 9 is a HPLC chromatogram of mice serum three minutes after intranasal administration of 20 μL of a control solution containing 4% by weight of aminophylline in accordance with the present invention.
Figure 10:
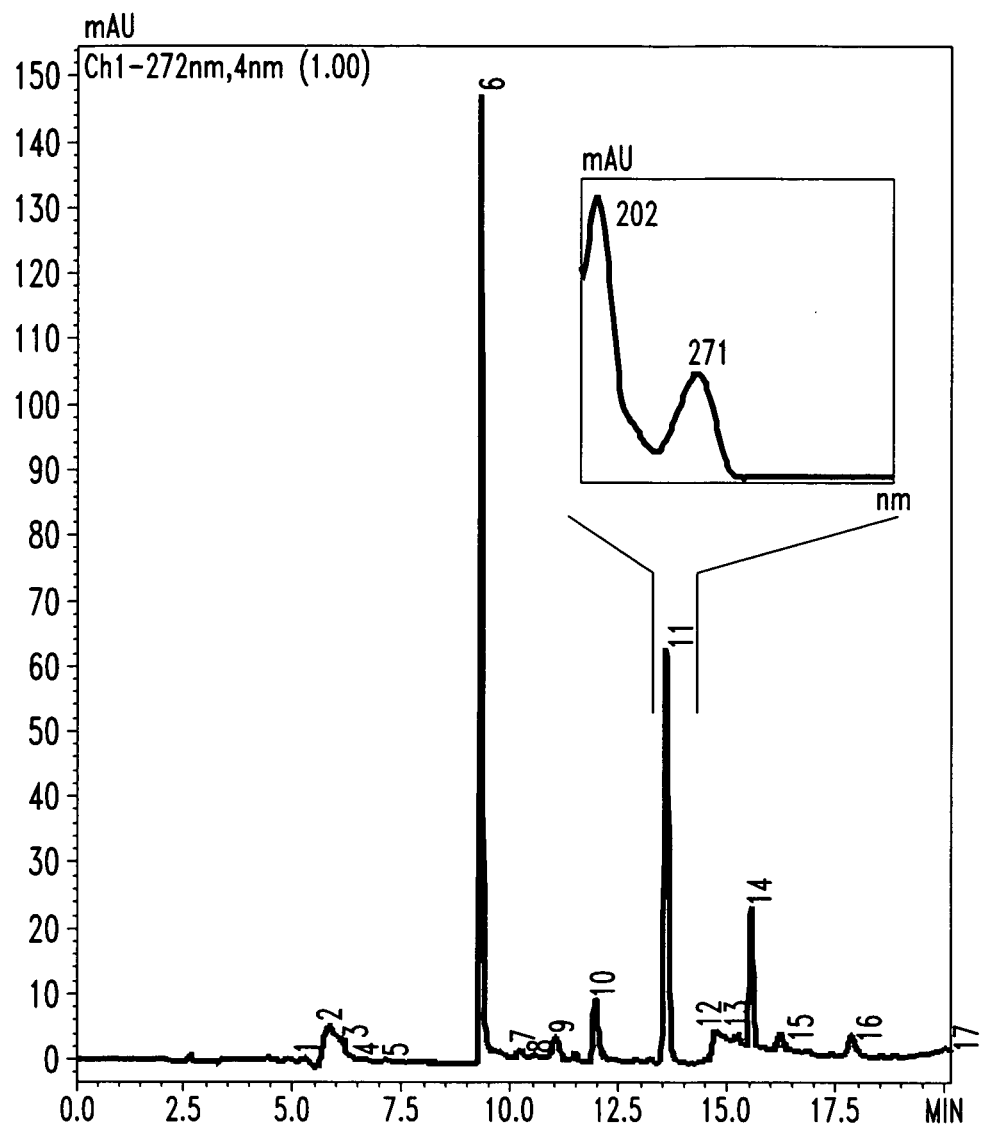
FIG. 10 is a HPLC chromatogram of mice serum three minutes after intranasal administration of 20 μL of a control solution containing 24% by weight of aminophylline in accordance with the present invention.

The chromatograms of serums from Controls 1 and 2 with aminophylline concentration of 4% by weight and 24% by weight are shown in FIGS. 9 and 10, respectively. Similar chromatograms were prepared for all of the samples. The areas of the aminophylline peaks that are proportional to its concentration in the blood taken from the retro-orbital sinus, are presented in Table 6 below:

TABLE 6

| Sample ID | Aminophylline Concentration in aqueous solution (% Wt) | Alkaloid/ Polyphenol/ Polymer Weight Ratio | Aminophylline Concentration in Blood Serum (µg/ml) |
|---|---|---|---|
| Control-1 | 4.0 | — | 19.91 |
| Control-2 | 24.0 | — | 20.09 |
| Formulation 1 | 4.0 | 1:1:8 | 6.26 |
| Formulation 2 | 4.0 | 1:2:8 | 5.87 |
| Formulation 3 | 4.0 | 1:3:8 | 3.39 |
| Formulation 4 | 2.0 | 1:2:8 | 15.20 |

The results shown in Table 6 for Control 1 and Control 2 indicate that absorption of the alkaloid from nasal mucous membrane into the bloodstream is not dependent on the concentration of alkaloid during administration but rather depends on the condition of the nasal mucous membrane area.

Abuse-resistant properties of the present compositions relative to abuse by snorting are evident by comparing the results of the tests for Formulations 1, 2 and 3 with the results from Control-1. The addition of polyphenol and water soluble polymer significantly reduces absorption of the alkaloid into the bloodstream. The level of reduction depends on the concentration of the polyphenol in the present composition. At an alkaloid to polyphenol ratio of 1:1 (Formulation 1) the alkaloid concentration in the blood was reduced by a factor of about 3, while at 1:3 ratio (Formulation 3) the reduction was 6-fold.

Dilution of the administered solution with water to reduce the concentration of aminophylline from 4.0% wt to 2.0% wt (compare Formulation 2 to Formulation 4) resulted in a sharp increase in the absorption rate. This increase in absorption rate is attributed to the corresponding decrease in the concentration of the polyphenol. The tests show that as concentration of the polyphenol increases, the more profound the effect of the present composition has on preventing abuse via snorting. Accordingly, there is a strong correlation between the concentration of polyphenol in the composition and the level of protection against abuse through snorting. Since abuse through snorting typically involves dry powder forms of the composition, the protection against abuse is maximized due to the higher concentration of polyphenol.

The results of the analysis of the alkaloid concentration in mice blood serum after intranasal administration of an alkaloid containing solution and an alkaloid-diversion-and-abuse-resistant solution, show that using the composition of the present invention, reduces alkaloid intake through nasal mucous membranes by at least a factor of 5. Concentration of the polyphenol at the mucous membrane exhibits a greater effect in determining the alkaloid concentration in the blood serum than concentration of the alkaloid in the dose administered. The results indicate that the absorption limiting effect is more profound when the composition is in a dry powder form. The results demonstrate the abuse-resistant properties of the present composition through nasal administration (e.g., snorting).

Example 8

Verification of Abuse-Resistant Properties of the Present Compositions Against Recreational Abuse Through Overdosing To demonstrate abuse-resistant properties of the present composition, an aqueous composition was prepared containing 4% aminophylline. The weight ratio of alkaloid:tannins:polyethylene glycol (4000 Da) was 1:1:8.

Figure 11:
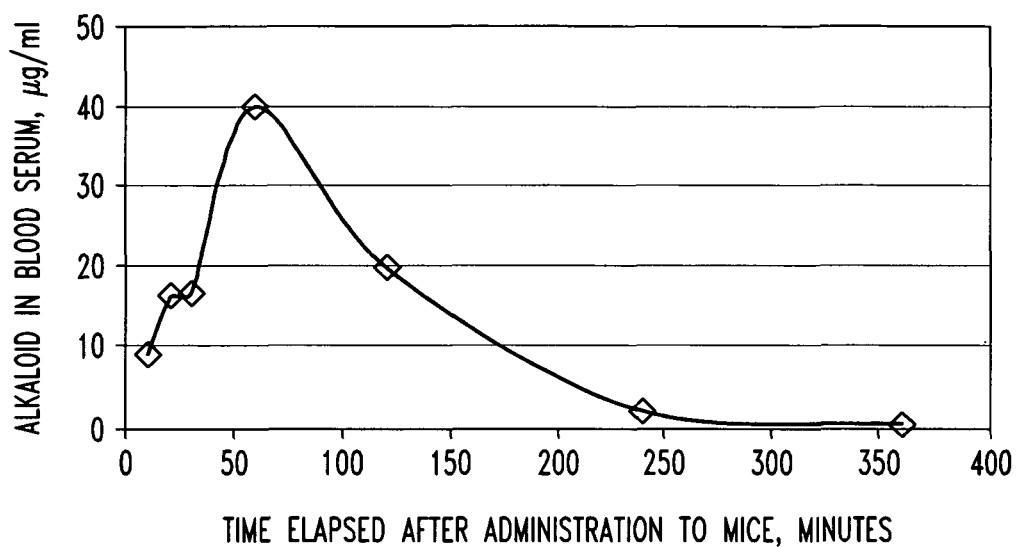
FIG. 11 is a graph showing alkaloid concentration in mice blood serum over time after oral administration of an abuse-resistant composition in accordance with the present invention.

First a pharmaco-dynamic profile of aminophylline was obtained following oral administration of the prepared formulation to male mice (CBA C50 Black F1 line), each having an average weight of about 30 g to 40 g. 50 µL of each experimental solution described above, was administered to a corresponding pool of three mice. Blood samples were collected under anesthesia following decapitation. The method of serum sample preparation was identical to the one described in the Example 7 with the exception that the blood samples were taken during the phase of stomach absorption (5 and 10 minutes after administration), the phase of duodenum absorption (20 and 30 minutes), the phase of upper and middle intestine absorption (1 and 2 hours after administration), and the phase of middle and distal intestine absorption (4 and 6 hours after administration). The results are shown in FIG. 11.

The results show that aminophylline is detected in just 5 minutes after oral administration, with a maximum concentration of aminophylline obtained after about 1 hour. After 6 hours only traces of the alkaloid was found. This is a classic pharmaco-dynamic profile for a free alkaloid that confirms the bioequivalency of the composition of the present invention.

The following solutions were prepared to investigate abuse-resistant properties of the present composition as shown in Table 7 below.

TABLE 7

| Sample ID | Aminophylline Concentration in aqueous solution (% Wt) | Alkaloid/Polyphenol/Polymer Weight Ratio |
|---|---|---|
| Formulation 5 | 0.6 | 1:1:8 |
| Formulation 6 | 1.1 | 1:1:8 |
| Formulation 7 | 2.0 | 1:1:8 |
| Formulation 8 | 4.0 | 1:1:8 |

The prepared formulations were administered to mice orally as a single 50 µL dose. Blood samples were collected 10 and 120 minutes after administration and prepared and analyzed following the procedures described in Example 7. The results are shown below in Table 8.

TABLE 8

Aminophylline Concentration in Blood Serum (μg/ml)

| Sample ID | 10 min | 120 min |
|---|---|---|
| Formulation 5 | 5.77 | 1.20 |
| Formulation 6 | 8.28 | 4.79 |
| Formulation 7 | 9.40 | 14.57 |
| Formulation 8 | 8.94 | 19.67 |

Figure 12:
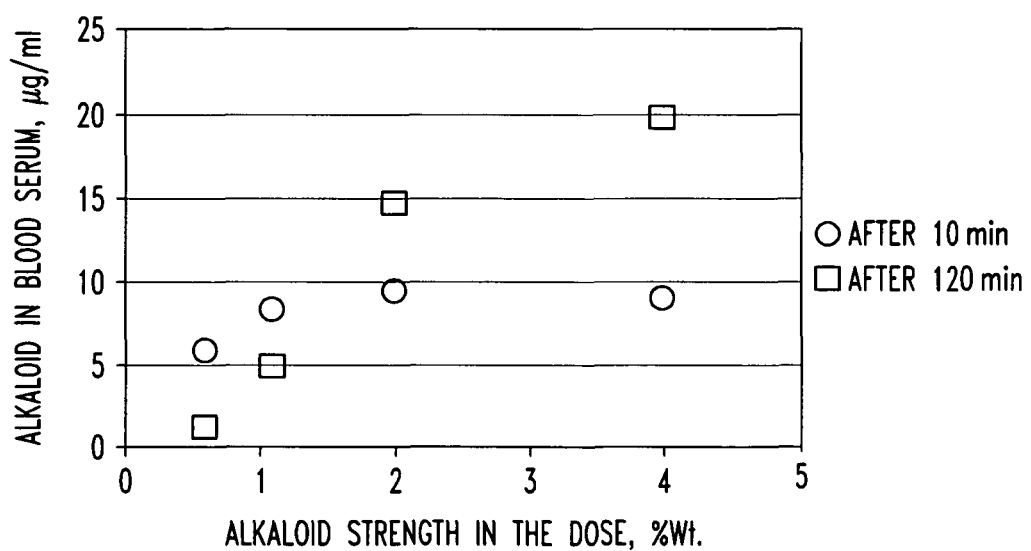
FIG. 12 is a graph showing alkaloid concentration in mice blood serum, respectively, at 10 minutes and 120 minutes

The results clearly indicate the abuse-resistant properties of the present invention. As the alkaloid dose level increased, the alkaloid level in the blood did not increase proportionally during stomach absorption phase (see circle data points of FIG. 12) within the entire range of dosing levels. The same effect, although not as pronounced, was also observed for higher doses during the upper intestine absorption phase (see square data points of FIG. 12). It is noted that the less pronounced effect observed during the upper intestine absorption phase may be related to the differences between the volume and dilution rate of the intestine and the stomach, which affect the actual concentration of both the alkaloid and the polyphenol.

It is important to mention that the increase in absorption of Formulation 8 over Formulation 7 was not proportional to the increase in alkaloid dose. The dose level was increased two-fold, but the absorption rate increased only by 30%. The data indicates that at low level doses the present composition performed similarly to a typical alkaloid-containing drug, and at high level doses absorption was compromised.

The results of the analysis of the alkaloid concentration in mice blood after oral administration of an alkaloid containing solution and an alkaloid-diversion-and-abuse-resistant solution, showed that using the composition of the present invention, significantly reduces the alkaloid intake through stomach membranes. The results also showed that this effect is more profound as intake of the alkaloid increases progressively. The results support the abuse-resistant properties of the present composition through overdosing means.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A composition comprising:
(a) at least one acid salt of an opioid active pharmaceutical ingredient (API);
(b) a first compound coupled to the acid salt of the opioid API to form a water-insoluble complex, and enabling the first compound to undergo oxidization under basic conditions, to form a fine particulate precipitate; and
(c) a second compound in an amount sufficient for coupling to the first compound in an aqueous environment, whereby the acid salt of the opioid API is released from the complex.

2. The composition of claim 1 wherein the first compound is astringent.

3. The composition of claim 1 wherein the an acid salt of an opioid API is a hydrochloric acid salt.

4. The composition of claim 3 wherein the opioid is natural, synthetic, semi-synthetic or combinations thereof.

5. A composition comprising:
an acid salt of an opioid active pharmaceutical ingredient at least one polyphenol, said acid salt and said polyphenol forming a water-insoluble complex; and
at least one water soluble polymer.

6. The composition of claim 5 wherein the polyphenol is selected from the group consisting of hydrolysable tannins, phenylpropanoids, compounds having at least one phenolic subcomponent selected from the group consisting of phenols, pyrocatechols, pyrogallols, resorcinol, phloroglucinol, and hydroquinone, and combinations thereof.

7. The composition of claim 5 wherein the polyphenol is selected from the group consisting of tannins, tannic acid, gallic acid, and combinations thereof.

8. The composition of claim 5 wherein the water soluble polymer is selected from the group consisting of polyalkyleneoxides, polyvinyl pyrrolidone, and combinations thereof.

9. The composition of claim 8 wherein the polyalkyleneoxides are selected from the group consisting of polyethylene glycol, polypropylene glycol, and combinations thereof.

10. The composition of claim 9 wherein the polyethylene glycol has a molecular weight of from about 400 Da to 400,000 Da.

11. The composition of claim 5 wherein the polyphenol is astringent.

12. The composition of claim 5 wherein the polyphenol is natural, synthetic, semi-synthetic or combinations thereof.

13. The composition of claim 5, wherein the acid salt of an opioid active pharmaceutical ingredient comprises oxycodone hydrochloride, the polyphenol comprises tannic acid, the water soluble polymer comprises polyethylene glycol, and the oxycodone hydrochloride, polyphenol and water soluble polymer are present in a weight ratio of about 1:1:7.

14. The composition of claim 1 wherein the sum of the amounts of the first compound and the second compound exceed the amount of the acid salt of the API.

15. The composition of claim 1 wherein the weight ratio of the (a):(b):(c) is in the range of from about 1:1-10:1-30.

16. The composition of claim 15 wherein the weight ratio is from about 1:1-3:5-10.

17. The composition of claim 16 wherein the weight ratio is about 1:1:7.

18. The composition of claim 1 wherein the opioid is selected from the group consisting of opiates and combinations thereof.

19. The composition of claim 1 wherein the acid salt of an opioid API comprises a compound selected from the group consisting of: oxycodone hydrochloride, morphine hydrochloride, hydrocodone hydrochloride, oxymorphone hydrochloride, and combinations thereof.

20. The composition of claim 1 where in active pharmaceutical ingredient comprises oxycodone hydrochloride, the first compound comprises tannic acid and the second compound comprises polyethylene glycol.

21. The composition of claim 20 further comprising a surfactant.

22. The composition of claim 21 in the form of a capsule.

23. The composition of claim 1 wherein the weight ratio of the (a)•(b)•(c) is in the range of about 1:0.5-10:0.5-30.

24. A pharmaceutical composition for administration to a warm-blooded animal for release of an opioid active pharmaceutical active (API) for a therapeutic purpose, comprising:
(a) a therapeutically effective amount of at least one acid salt of an opioid API;
(b) a first compound coupled to the acid salt of the opioid API to form a water-insoluble complex enabling the first compound to undergo oxidization under basic conditions, to form a fine particulate precipitate;

(c) a second compound in an amount sufficient for preferentially coupling to the first compound in an aqueous environment, whereby the acid salt of the API is released from the complex; and (d) a pharmaceutically acceptable carrier.

25. The pharmaceutical composition of claim 24 wherein the first compound is astringent.

26. The pharmaceutical composition of claim 24 wherein the API is selected from the group consisting of: oxycodone hydrochloride, morphine hydrochloride, hydrocodone hydrochloride, oxymorphone hydrochloride, and combinations thereof.

27. The pharmaceutical composition of claim 24 wherein the first compound is at least one polyphenol.

28. The pharmaceutical composition of claim 24 wherein the second compound is at least one water soluble polymer.

29. The pharmaceutical composition of claim 24 further comprising at least one additive selected from the group consisting of surfactants, gel forming compounds, and combinations thereof.

30. The pharmaceutical composition of claim 24 in the form of tablets, soft capsules, hard capsules, gels, and liquid formulations.

31. A pharmaceutical composition for administration to a warm-blooded animal for release of an opioid active pharmaceutical ingredient (API) for a therapeutic purpose comprising:

a first complex comprising an opioid acid salt of an API bound to a polyphenol, said polyphenol being capable of undergoing oxidation under basic conditions to form a fine particulate precipitate;

a water soluble polymer in an amount sufficient for preferentially binding to the polyphenol in an aqueous environment, whereby the acid salt of the API of the first complex is released from said first complex.

32. The pharmaceutical composition of claim 31 wherein the polyphenol is astringent.

33. The pharmaceutical composition of claim 31 wherein the API is selected from the group consisting of: oxycodone hydrochloride, morphine hydrochloride, hydrocodone hydrochloride, oxymorphone hydrochloride, and combinations thereof.

34. The pharmaceutical composition of claim 31 wherein the water soluble polymer preferentially binds to the polyphenol in an acidic or slightly basic environment.

* * * * *